United States Patent
Frantz et al.

(10) Patent No.: US 11,185,436 B2
(45) Date of Patent: Nov. 30, 2021

(54) METHODS AND SYSTEM FOR HOMOGENEOUS DENTAL APPLIANCE

(71) Applicant: FRANTZ DESIGN INCORPORATED, Austin, TX (US)

(72) Inventors: Joseph Lee Frantz, Austin, TX (US); Donald E Frantz, Katy, TX (US)

(73) Assignee: Frantz Design Inc., Spicewood, TX (US)

( * ) Notice: Subject to any disclaimer, the term of this patent is extended or adjusted under 35 U.S.C. 154(b) by 0 days.

(21) Appl. No.: 16/631,160

(22) PCT Filed: May 30, 2019

(86) PCT No.: PCT/US2019/034647
§ 371 (c)(1),
(2) Date: Jan. 14, 2020

(87) PCT Pub. No.: WO2019/232205
PCT Pub. Date: Dec. 5, 2019

(65) Prior Publication Data
US 2020/0214877 A1 Jul. 9, 2020

Related U.S. Application Data

(60) Provisional application No. 62/679,007, filed on May 31, 2018.

(51) Int. Cl.
*A61F 5/56* (2006.01)
*B29C 64/00* (2017.01)
(Continued)

(52) U.S. Cl.
CPC ............. *A61F 5/56* (2013.01); *A61C 7/08* (2013.01); *A61C 7/36* (2013.01); *B29C 45/00* (2013.01); *B29C 51/10* (2013.01); *B29C 64/00* (2017.08)

(58) Field of Classification Search
CPC ...... A61F 5/566; A61F 5/56; A61F 2005/563; A61F 5/58; A61C 7/08; A61C 19/063;
(Continued)

(56) References Cited

U.S. PATENT DOCUMENTS

| 2003/0049584 A1 | 3/2003 | Chishti et al. |
| 2004/0214127 A1 | 10/2004 | Kubo et al. |

(Continued)

FOREIGN PATENT DOCUMENTS

WO WO2010/0043805 11/2016

*Primary Examiner* — Ophelia A Hawthorne
(74) *Attorney, Agent, or Firm* — Anderson Law Group LLC; Margaret M. Anderson

(57) ABSTRACT

Methods and systems herein relate to receiving dentition data of a patient; processing the dentition data in a server to determine a vertical displacement and a forward mandibular position to enable the patient to breathe during sleep by opening the airway of the patient; and forming a homogeneous dental appliance via direct manufacture using the processed dentition data, the vertical displacement and the forward mandibular position, the dental appliance including a lower dental tray and an upper dental tray, the lower dental tray inclusive of a pair of vertical displacement bite pads with the vertical displacement and a first pair of button protrusions, the upper dental tray inclusive of a second pair of button protrusions, the first pair of button protrusions and the second pair of button protrusions providing the forward mandibular position when two elastic bands are attached to connect the upper dental tray and the lower dental tray.

10 Claims, 13 Drawing Sheets

(51) Int. Cl.
  *A61C 7/08* (2006.01)
  *A61C 7/36* (2006.01)
  *B29C 51/10* (2006.01)
  *B29C 45/00* (2006.01)

(58) Field of Classification Search
  CPC ....... A61C 7/36; A61B 5/4547; A61B 5/4552;
    A61B 5/4557; A61B 5/682; A61B
    5/0534; A61B 71/085; A61B 2071/086;
    A61B 2017/088; B29C 64/00; B29C
    64/386; B29C 69/001; B29C 64/118;
    B29C 64/112; B29C 51/10; B29C 51/46;
    B29C 45/00; B33Y 10/00; B33Y 30/00;
    B33Y 50/02; B29K 2105/256; B29L
    2031/753; B32B 27/32; B32B 27/08;
    B32B 2250/24; B32B 37/153; B32B
    2250/03; B32B 2250/05; B32B 2307/31;
    B32B 7/02; B32B 5/26; B32B 2250/02;
    B32B 2250/04; B32B 2307/72; B32B
    2307/728; B32B 2307/73; B32B
    2307/738; B32B 2309/02
  See application file for complete search history.

(56) References Cited

U.S. PATENT DOCUMENTS

| | | |
|---|---|---|
| 2009/0287332 A1 | 11/2009 | Adusumilli et al. |
| 2010/0043805 A1 | 2/2010 | Kelly |
| 2011/0223565 A1 | 9/2011 | Ando |
| 2013/0095446 A1 | 4/2013 | Andreiko et al. |
| 2015/0059766 A1 | 3/2015 | Frantz et al. |
| 2017/0224441 A1* | 8/2017 | Anderson ................ A61B 1/24 |

* cited by examiner

METHODS AND SYSTEM FOR HOMOGENEOUS DENTAL APPLIANCE

CROSS-REFERENCE TO RELATED APPLICATIONS

The present application is a non-provisional filing of, and claims benefit under 35 U.S.C. § 119(e) from, U.S. Provisional Patent Application Ser. No. 62/679,007, entitled "Methods and System for Homogeneous Dental Appliance," filed May 31, 2018, which is hereby incorporated by reference in its entirety.

BACKGROUND

Sleep apnea and obstructive sleep apnea treatments include surgery, positive airflow machinery, such as CPAP machines, and dental appliances. One known dental appliance is the "Elastic Mandiblular Advancement" (EMA®) and related appliances. The EMA® appliance operates by providing increased airflow by forward mandibular advancement. One problem with the EMA® appliance is the risk that button protrusions that attach to elastic bands on each side of the appliance will detach from the appliance. One method of attaching the button protrusions on each side of the appliance includes cementing. However, cementing the button protrusions can result in detachment over time and with increased use. What is needed is a dental appliance that has a lower risk of button protrusion detachment.

SUMMARY

Some embodiments of a method may include receiving oral characteristic data of a patient; processing the oral characteristic data in a server to determine dentition data, a vertical displacement and a forward mandibular position to enable the patient to breathe during sleep by opening an airway of the patient; and forming a dental appliance via direct manufacture using the dentition data, the vertical displacement and the forward mandibular position, the dental appliance including a lower dental tray and an upper dental tray, each of the lower dental tray and the upper dental tray being homogeneous, the lower dental tray inclusive of the vertical displacement and a first pair of button protrusions, the upper dental tray inclusive of a second pair of button protrusions, the first pair of button protrusions and the second pair of button protrusions providing the forward mandibular position when two elastic bands are attached to connect the upper dental tray and the lower dental tray.

In one or more embodiments, the dental appliance is formed by three-dimensional (3D) printing of one or more of a light polymerizable liquid thermoset crosslinked polymer, a polyurethane, a methacrylate or a copolymer.

In one or more embodiments, the dental appliance is formed by three-dimensional (3D) printing of a polymerizable resin composition of a urethane monomer of urethane dimethacrylate (UDMA), an acidic monomer, and one or more hydrophobic monomers.

In one or more embodiments, the dental appliance is milled or injection molded from one or more of an Ethylene Propylene Copolymer and a Polyoxymethlene Copolymer.

In one or more embodiments, the dental appliance is injection molded using one or more of thermoplastic olefin, thermoplastic polyolefin, and olefinic thermoplastic elastomer.

In one or more embodiments receiving oral characteristic data of the patient includes scanning by a scanner or camera a mold of the teeth; and transmitting the oral characteristic data to a server.

In one or more embodiments receiving oral characteristic data of a patient includes scanning by a scanner of an oral cavity of the patient; imaging the oral cavity to determine the dentition data, wherein the oral characteristic data includes dentition data as one or more images of teeth and a gum line of the patient and one or more images of a soft palate of the patient; and transmitting the oral characteristic to a server.

In one or more embodiments the method includes determining via the oral characteristic data the vertical displacement as a function of a shape of the soft palate of the patient.

In one or more embodiments the determining via the oral characteristic the vertical displacement as a function of the shape of the soft palate of the patient includes determining a vertical displacement of between 5 and 7 millimeters if the soft palate has between 5 to 7 millimeters of space between a posterior edge of the soft palate to a posterior wall of an oral pharynx of the patient.

In one or more embodiments, the determining via the oral characteristic data the vertical displacement as a function of the shape of the soft palate of the patient includes processing the oral characteristic data to measure a distance from a gingival-tooth crown juncture of a maxillary central to a gingival-tooth crown juncture of a mandibular central.

In one or more embodiments the determining via the oral characteristic data the vertical displacement as a function of the shape of the soft palate of the patient includes determining if a posterior edge of the soft palate is longer than a normal soft palate with between 3 and 5 millimeters of space between a posterior edge of the soft palate to a posterior wall of an oral pharynx of the patient; and providing the vertical displacement of between 8 and 10 millimeters.

In one or more embodiments the determining via the oral characteristic data the vertical displacement as a function of the shape of the soft palate of the patient includes determining if a posterior edge of the soft palate is longer than a normal soft palate and webbed and wherein two millimeters or less of space exists between the soft palate and a posterior wall of an oral pharynx, providing at least 11 to 14 millimeters for the vertical displacement.

In one or more embodiments the determining via the oral characteristic data the vertical displacement as a function of the shape of the soft palate of the patient includes determining whether the soft palate is one of short, normal, and long.

In one or more embodiments the lower dental tray is inclusive of a first vertical displacement bite pad on a left side of the lower dental tray and a second vertical displacement bite pad on a right side of the lower dental tray wherein a height of each of the first and second vertical displacement bite pads is determined according to the oral characteristic data, the oral characteristic data providing soft tissue data of the patient indicative of airway function.

In one or more embodiments the vertical displacement is provided by a thickness of the lower dental tray.

Another embodiment is directed to a system including a processor and a non-transitory computer-readable storage medium storing instructions operative when executed on the processor to perform a method including receiving oral characteristic data of a patient; processing the oral characteristic data in a server to determine dentition data, a vertical displacement and a forward mandibular position to enable the patient to breathe during sleep by opening an airway of the patient; and forming a dental appliance via direct manufacture using the dentition data, the vertical displacement and the forward mandibular position, the dental appliance including a lower dental tray and an upper dental tray, each of the lower dental tray and the upper dental tray being homogeneous, the lower dental tray inclusive of a vertical displacement bite pad with the vertical displacement and a first pair of button protrusions, the upper dental tray inclusive of a second pair of button protrusions, the first pair of button protrusions and the second pair of button protrusions providing the forward mandibular position when two elastic bands are attached to connect the upper dental tray and the lower dental tray.

Another embodiment is directed to a method including receiving, by a server, one or more data sets associated with a patient; determining, by the server one or more positions for placement of button protrusions based on the received data sets from a scanner, the received data sets including at least a dentition pattern, a gum line, a soft palate measurement of a soft palate shape of the patient and a uvula placement measurement with respect to the palate shape of the patient; communicating, by the server the one or more positions for placement of button protrusions and a vertical displacement, the communicating including assigning a value associated with each of the one or more positions for placement of button protrusions, each value representative of a distance between an upper tray button protrusion and a lower tray button protrusion for mandibular advancement; transmitting the value data to one or more of a three-dimensional printer, a milling apparatus and an injection molding apparatus; forming a dental appliance via direct manufacture using the value associated with each of the one or more positions for placement of button protrusions, the dental appliance including a lower dental tray and an upper dental tray, each of the lower dental tray and the upper dental tray being homogeneous, the lower dental tray inclusive of the vertical displacement and a first pair of the button protrusions, the upper dental tray inclusive of a second pair of the button protrusions, the first pair of button protrusions and the second pair of button protrusions providing the forward mandibular position when two elastic bands are attached to connect the upper dental tray and the lower dental tray.

In one or more embodiments, the dental appliance is formed by three-dimensional (3D) printing of one or more of a light polymerizable liquid thermoset crosslinked polymer, a polyurethane, a methacrylate and a copolymer.

In one or more embodiments, the dental appliance is one or more of milled and injection molded using one or more of an Ethylene Propylene Copolymer and a Polyoxymethlene Copolymer.

In one or more embodiments, the dental appliance is formed by three-dimensional (3D) printing of a polymerizable resin composition of a urethane monomer of urethane dimethacrylate (UDMA), an acidic monomer, and one or more hydrophobic monomers.

In one or more embodiments, the dental appliance is injection molded using a thermoplastic olefin, thermoplastic polyolefin, or olefinic thermoplastic elastomer.

In one or more embodiments, the vertical displacement is a function of the soft palate shape of the patient.

In one or more embodiments, the vertical displacement is provided by one or more of a pair of bite pads on the lower dental tray or by a thickness of the lower dental tray.

In one or more embodiments, the gum line determination identifies a maxillary tooth crown-gingival junction and a mandibular tooth crown-gingival junction, the upper dental tray is formed to reach about a three millimeter distance below the maxillary tooth crown-gingival junction on the upper dental tray, and the lower dental tray is formed to reach about three millimeters below the mandibular tooth crown-gingival junction.

Some embodiments include a processor and a non-transitory computer-readable storage medium storing instructions operative when executed on the processor to perform the methods herein described.

DETAILED DESCRIPTION

Figure 1A:
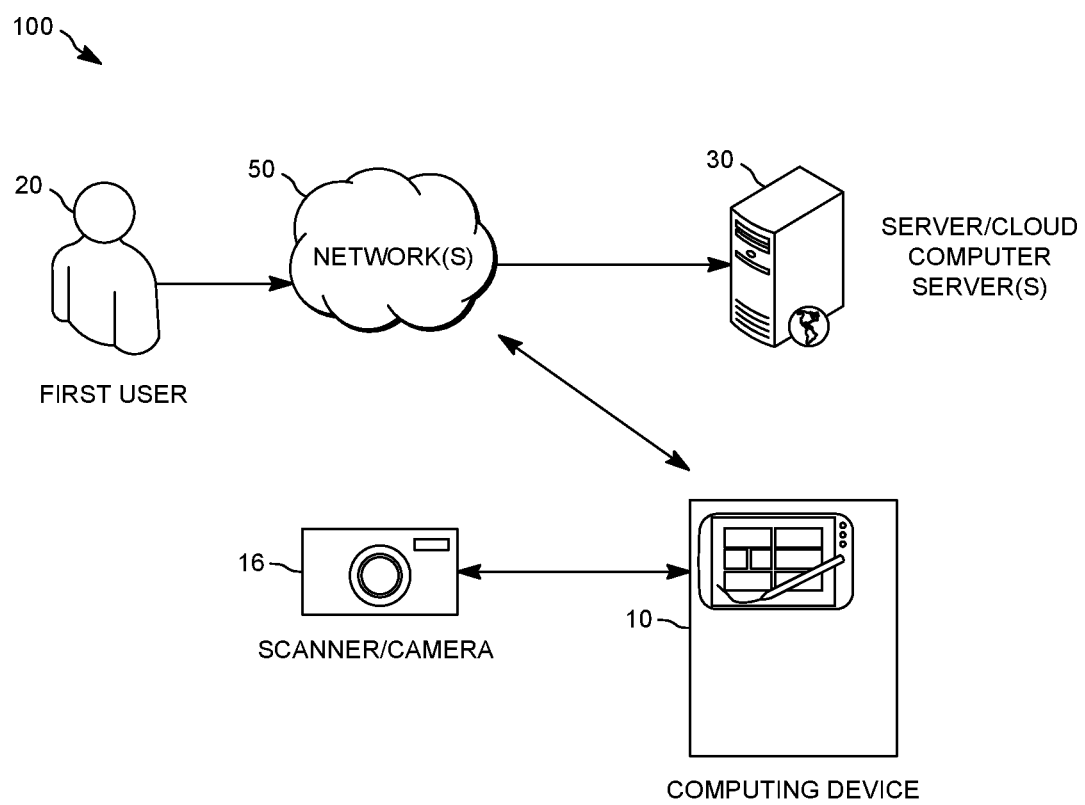
FIG. 1A illustrates a system and network environment including a computing device in accordance with one or more embodiments of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring now to FIG. 1A, the figure illustrates a computing device 10 connected via a network interface to a computer server 30 in an exemplary environment 100. As will be further described herein the illustrated computing device 10 and computer server 30 may employ the computationally implemented methods, systems, and articles of manufacture in accordance with various embodiments. The computing device 10 and computer server 30, in various embodiments, enable functions of the computing device 10.

Computing device 10 illustrated in FIG. 1A can be a tablet computer, in alternative embodiments, the computationally implemented methods, systems, and articles of manufacture in accordance with various embodiments may be embodied in other types of computer systems having other form factors including other types of portable computing devices such as, for example, mobile telephones, laptops, smartphones, e-readers, and so forth. Computing devices can include smartphones, client computers and the like as possible computing devices. As illustrated, the computing device 10 can include a display, such as a touchscreen as input/output of the computing device 10. Computing device 10 can further include a keyboard, either as a touch input/output keyboard or as an attached keyboard. As further depicted, the computing device 10 may also be connected to a scanner 16. In one embodiment, scanner 16 can be a scanning camera capable of creating a 3D image of teeth.

Figure 1B:
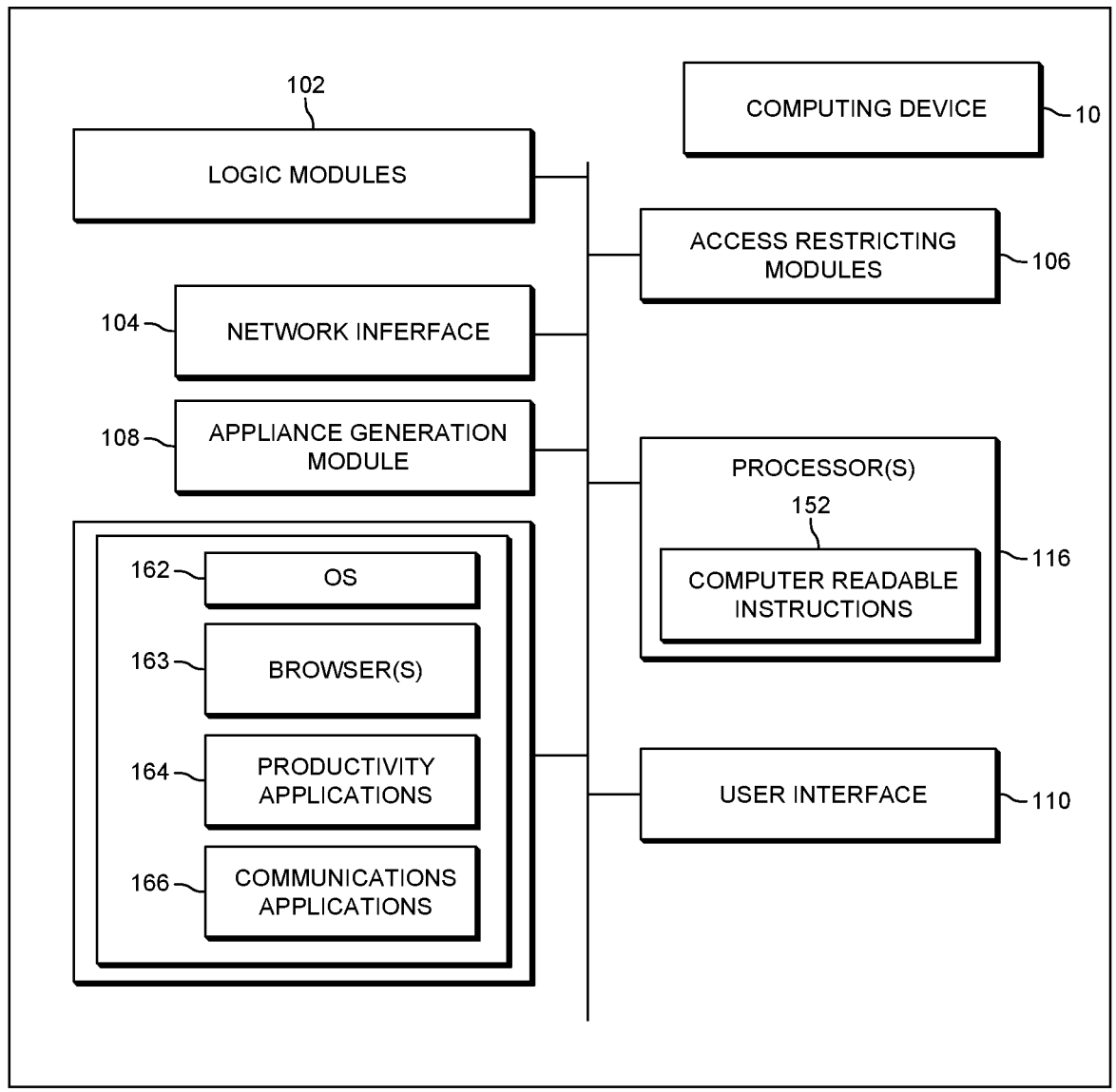
FIG. 1B illustrates a processor and a computing device in accordance with one or more embodiments of the present disclosure.

Referring now to FIG. 1B, computing device 10 is further illustrated with logic modules 102, network interface 104, user interface 110, processors 116 and memory 114. Logic modules 102 can be implemented using circuit components such as ASIC, logic modules 102 and other modules shown, may be implemented using a combination of specifically designed circuitry such as ASIC and one or more processors 116 (or other types of circuitry such as field programmable gate arrays or FPGAs) executing computer readable instructions 152. For example, in some embodiments, at least one of the logic modules may be implemented using specially designed circuitry (e.g., ASIC) while a second logic module may be implemented using a processor 116 (or other types of programmable circuitry such as an FPGA) executing computer readable instructions 152 (e.g., software and/or firmware). System requirements could dictate a combination of software and firmware and circuitry to meet the embodiments herein, for example, logic modules could be designed to use the most efficient combination of software/hardware/firmware in order to quickly implement methods and systems within the scope of the present disclosure. In some embodiments, a Computer-Aided Design/Computer-Aided Manufacture (CAD/CAM) program operates to implement methods herein for forming a dental appliance from scanned images. For example, a CAD program can create data in a three-dimensional format and transmit the data to a manufacturing device, such as a 3D printer, milling machine, or injection mold creation device. Methods herein include using patient-oriented oral characteristic data to determine placement of button protrusions and vertical displacement automatically by categorizing a patient's sleep apnea needs according to soft tissue characteristics and dentition. Soft tissue as described herein refers to soft palate, gum line, uvula placement as well as hyoid tissue and the like in an oral cavity of a patient.

In various embodiments, the memory 114 of the computing device 10 may comprise of one or more of mass storage device, read-only memory (ROM), programmable read-only memory (PROM), erasable programmable read-only memory (EPROM), cache memory such as random access memory (RAM), flash memory, synchronous random access memory (SRAM), dynamic random access memory (DRAM), and/or other types of memory devices. In various embodiments, the one or more applications 160 stored in memory 114 may include, for example, an operating system 162, a browser(s) 163, and one or more productivity applications 164 such as a word processing application or an imaging application, scanning application and one or more communication applications 166.

Computing device 10 may also include access restricting module 106. Access restricting module 106 of the computing device 10 can be configured to restrict access via the computing device 10 or preventing one or more actions by computing device 10. Computing device 10 may also include appliance generation module 108 coupled to access restricting module 106 via a bus.

Figure 2:
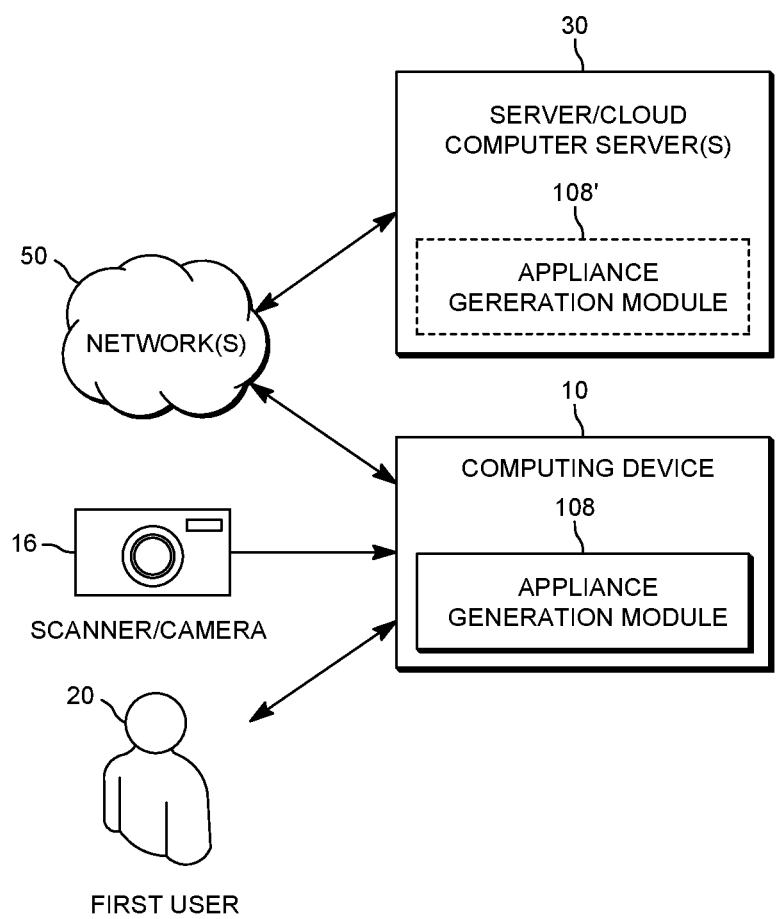
FIG. 2 illustrates a network environment in accordance with one or more embodiments of the present disclosure.

Referring to FIG. 2, appliance generation module 108 may be configured to determine that a first user 20 is an authorized user attempting to operate computing device 10. Appliance generation module 108 can also be configured to determine an established authorized user based on network received data while computing device 10 is connected to a network connection 50. In the case of appliance generation module 108, existing in a cloud computing setting or computer server 30, appliance generation module 108 may be configured to determine a network-based authorization for the first user when first logging into network 50 or cloud computing logging to computer server 30.

Appliance generation module 108 can be configured to receive inputs from a scanner 16. In some embodiments, appliance generation module 108 is coupled to a milling device, a three-dimensional printer, or an injection mold creation device. Appliance generation module 108 can receive CAD/CAM data or other oral characteristic data and/or dentition data to enable creation of a dental appliance in accordance with one or more embodiments herein.

Computer server 30 connecting via network 50 to the computing device 10 of FIGS. 1A and 1B can establish and/or determine a vertical displacement and a forward mandibular position for treating sleep apnea. For example, scanner 16 and/or molds of a patient's teeth can be examined and used to determine the adjustment needed for treating sleep apnea. Upper and lower trays including button protrusions can be created from molds. For instance, a patient with malocclusion and sleep apnea will require a determination via scanner 16 or other method. Each patient, depending on the results of scanned teeth and soft tissue and patient feedback, may require a different placement of horizontal and vertical displacement for both treating sleep apnea. Vertical displacement can be by way of lower bite pads or by way of the thickness of a lower dental tray. In embodiments, the vertical displacement is part of the mold, milled appliance or 3D printed dental appliance.

In one embodiment, the mold(s) enables pouring of an FDA approved material such as a thermoplastic material or nylon to form an upper and lower tray adapted to fit tightly but removably over upper and lower teeth such that the lower tray creates the forward mandibular position with respect to the upper tray when elastic material is releasably attached to the forward and the rearward portions of the opposite sides of the upper and lower trays, respectively, to enable the forward mandibular position of the lower tray with respect to the upper tray. Button protrusions on the lower dental tray and on the dental upper tray are arranged to enable elastic bands to attach thereto. In one embodiment, the button protrusions are included as part of the mold for injection molding, milled from a "puck" for the dental appliance trays, or directly manufactured during 3D printing.

One embodiment includes determining a dimension and elasticity for one or more removably attachable elastic bands adapted to connect the upper and lower tray via protrusions on each of the upper and the lower trays such that the elastic bands create the forward mandibular position of the lower tray with respect to the upper tray.

The elastic bands can include a plurality of pairs of elastic bands, each pair being of different length and/or elasticity.

Figure 3:
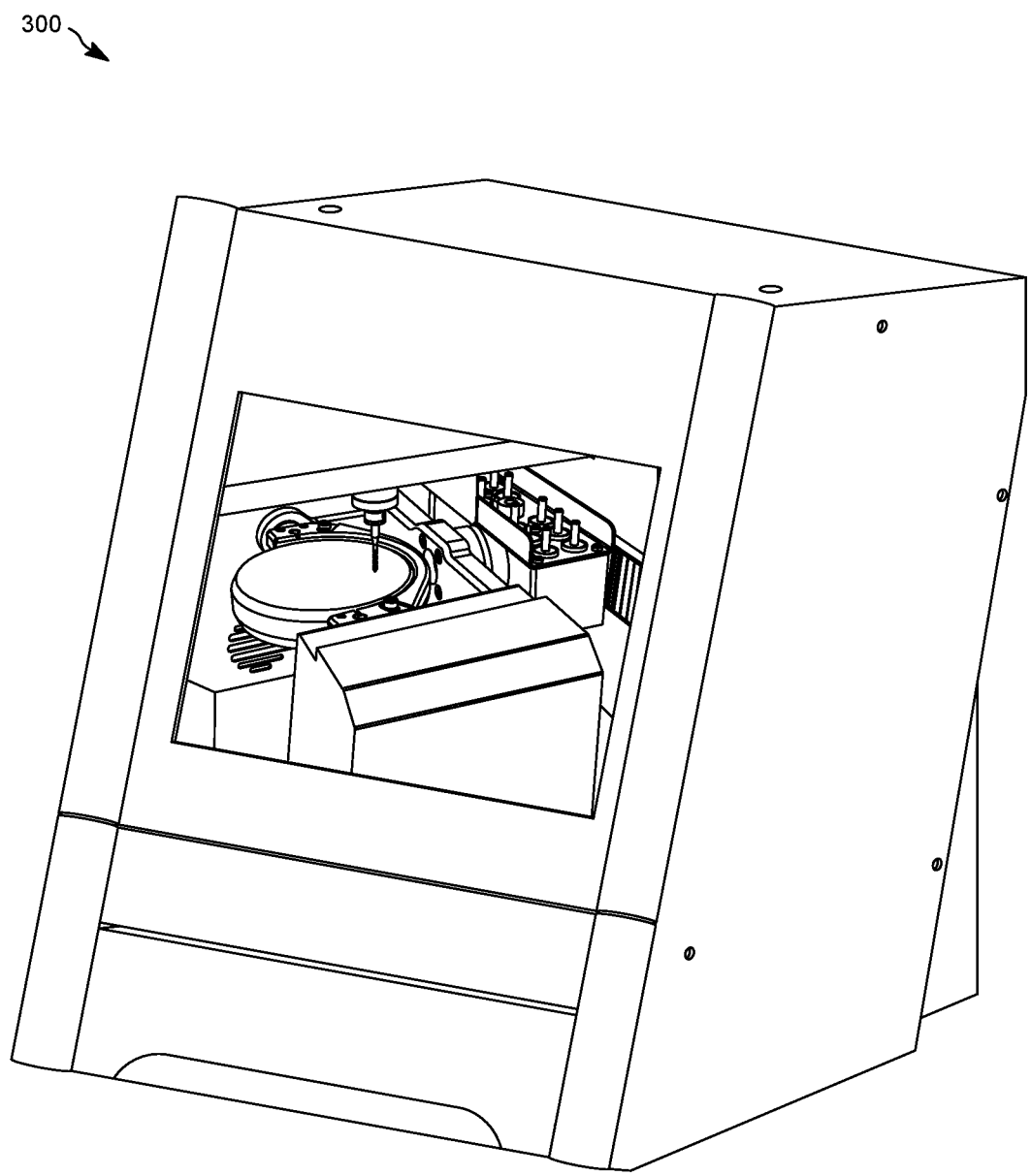
FIG. 3 illustrates a milling machine in accordance with one or more embodiments of the present disclosure.

In one embodiment, the dental appliance is configured to be worn during sleep. Referring now to FIG. 3, the dental appliance can include upper and lower trays that are manufactured using three-dimensional (3D) technologies such as 3D printing or 3D data collection via scanning or the like, that can be sent to a milling device 300, as shown in FIG. 3. The resulting dental appliance is shown in FIG. 4.

Figure 4:
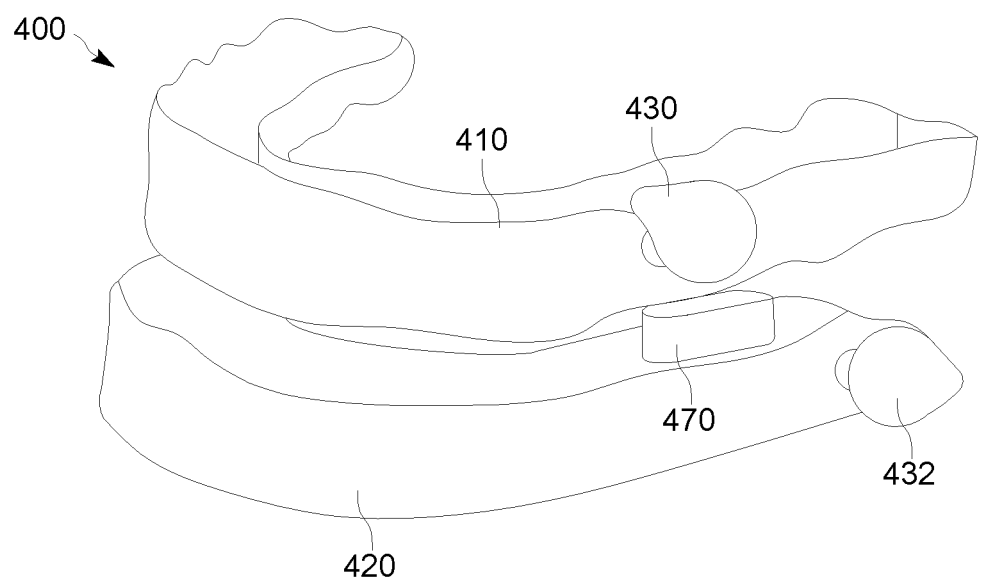
FIG. 4 illustrates a homogeneous dental appliance including button protrusions and a vertical displacement bite pad by direct manufacture in accordance with one or more embodiments of the present disclosure.

Referring now to FIG. 4, the dental appliance 400 is shown including an upper tray 410, lower tray 420, upper button protrusion 450, lower button protrusion 460 and bite pad 470. Unlike other dental appliances that include button protrusions and lower bite pads, embodiments herein include bite pads that are not integral with the lower button protrusion but are directly manufactured as part of the dental tray. Direct manufacture, as used herein refers to forming a dental appliance homogeneously in that different parts, such as button protrusions and vertical displacement bite pads appropriate for a patient are manufactured at the same time as the dental trays themselves and incorporated into either a mold, a milled material or printed by a three-dimensional printer.

The materials appropriate for a three-dimensional printer can be resin-type materials and materials described in U.S. Pat. No. 9,682,018 to Sadowsky et al., Jun. 20, 2017, "Denture Tooth and Material" which is hereby incorporated by reference in its entirety. As one of skill in the art will appreciate, materials appropriate for dental appliances must be FDA approved. Appropriate materials for resins is further described in Tanaka J, Hashimoto T., Stansbury J W, Antonucci J M, Suzuki K., "Polymer Properties of Resins Composed of UDMA an Methacrylates With the Carboxyl Group" Dental Material Journal 2001; 10:206-215, which incorporated by reference herein in its entirety.

Three-dimensional printing, as referred to herein include, but is not limited to, stereolithography (SLA), micro-stereolithography (pSLA), DLP projection, 2PP (two photon polymerization), continuous liquid interface production and material jetting. In embodiments, three-dimensional printing includes a layer-by-layer printing with successive layers formed in discrete layers. For example, a surface with a build plate immersed in a reservoir of a formulation of a polymer/resin component can be exposed to light at wavelengths and intensity to activate a photoinitiator to cause photopolymerization. As one of skill in the art will appreciate, there are other methods of three-dimensional printing such as continuous liquid interphase printing, in which dental trays are built up from a reservoir of photopolymerizable resin. Continuous liquid interphase printing is described in U.S. Patent Publication Nos. 2015/0097315, 2015/0097316, and 2015/0102532, the disclosures of each of which are incorporated herein by reference in their entirety.

Figure 5:
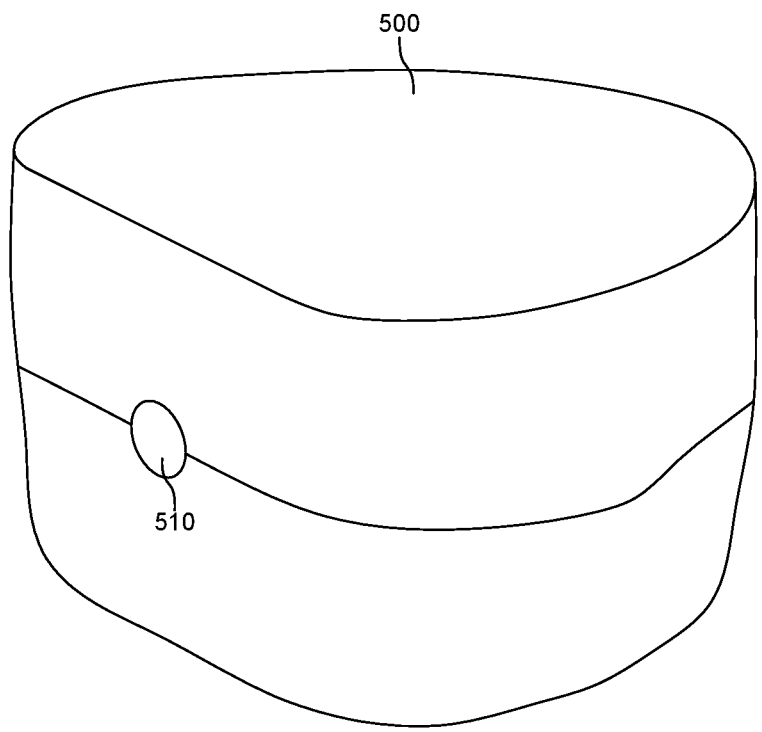
FIG. 5 illustrates an exemplary thermal injection mold for creating a homogeneous dental tray by direct manufacture in accordance with one or more embodiments of the present disclosure.

In some embodiments, the dental appliance can be formed via injection molding. For example, two molds such as mold 500 illustrated in FIG. 5 can be used to the upper and lower dental trays.

Figure 6:
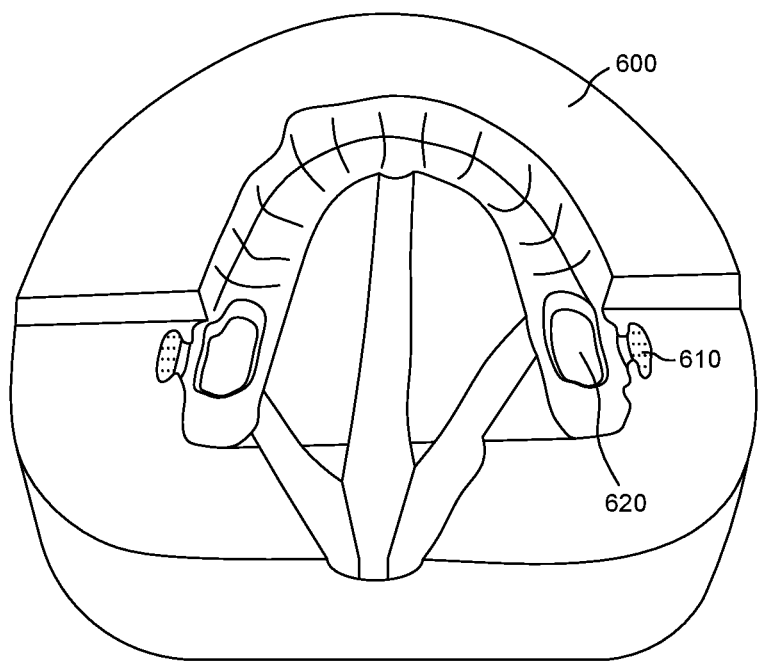
FIG. 6 illustrates a negative portion of a thermal injection mold for a bottom dental tray in accordance with one or more embodiments of the present disclosure.
Figure 7:
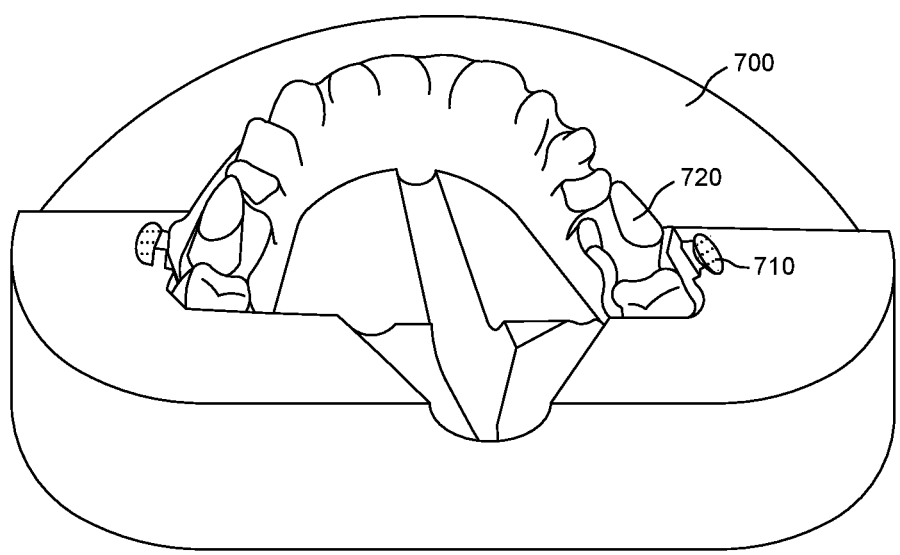
FIG. 7 illustrates a positive portion of a thermal injection mold for a bottom dental tray to be used with the mold of FIG. 6 in accordance with one or more embodiments of the present disclosure.

Referring now to FIG. 6, a portion of a mold illustrating a negative of a bottom dental tray 600 is illustrated. Specifically, mold 600 includes negative teeth 640, and negative button protrusions such as 610 and a negative for bite pads, such as 620. Referring now to FIG. 7, a positive mold for the bottom dental tray 700 is shown. Positive mold 700 includes button protrusions such as 710, bite pad 720 and teeth 740.

Figure 8:
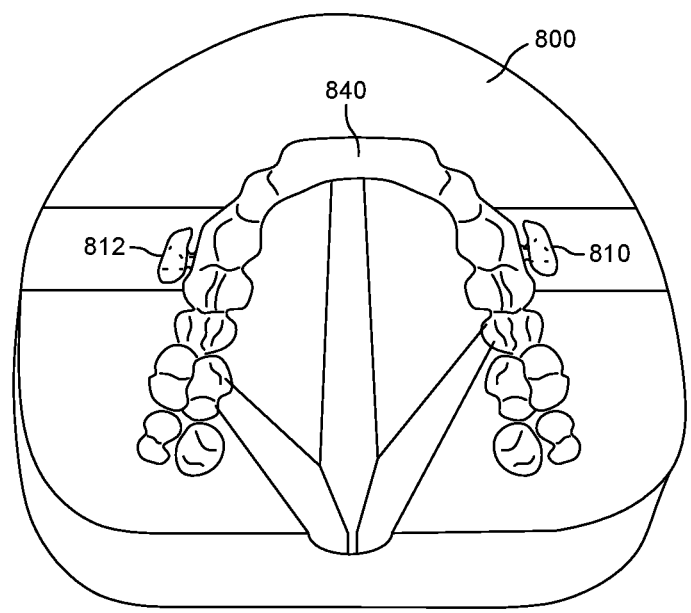
FIG. 8 illustrates a negative portion of a thermal injection mold for an upper dental tray in accordance with one or more embodiments of the present disclosure.
Figure 9:
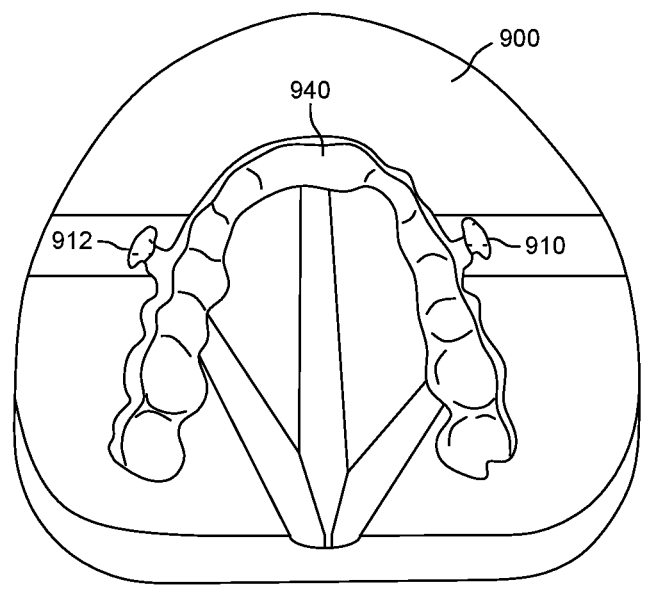
FIG. 9 illustrates a positive portion of a thermal injection mold for an upper dental tray to be used with mold of FIG. 8 in accordance with one or more embodiments of the present disclosure.

Referring now to FIG. 8, a similar mold to FIG. 6 is illustrated, showing a negative of an upper dental tray. As shown, negative mold 800 includes button protrusions 810, 812 and negative teeth 840. Referring to FIG. 9, a positive mold 900 for the upper dental tray is shown, including button protrusions 910, 912 and teeth 940.

Figure 10:
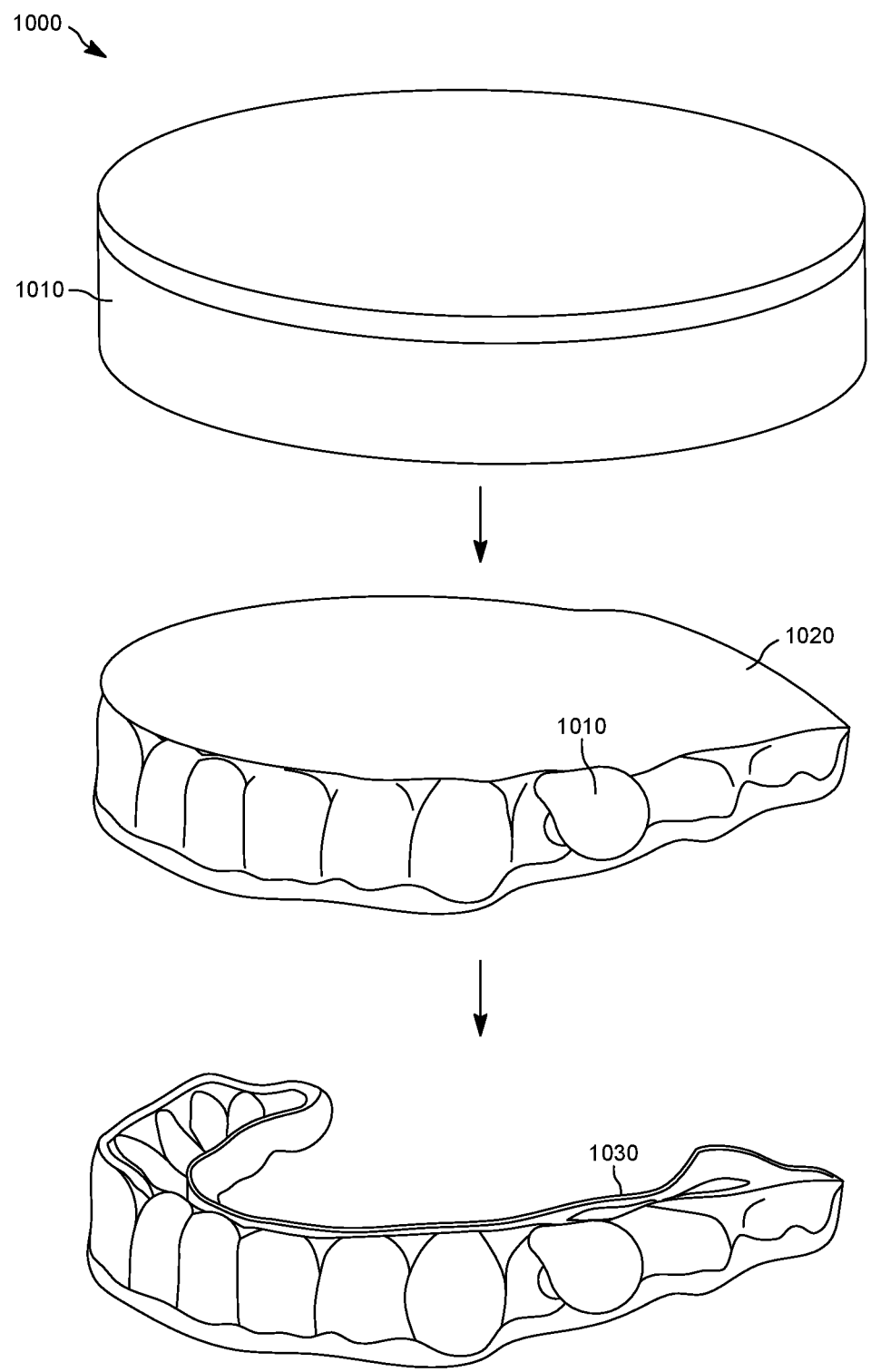
FIG. 10 illustrates a process for milling a solid material "puck" into a dental tray by direct manufacture in accordance with one or more embodiments of the present disclosure.

Referring now to FIG. 10, a milling process 1000 is shown including a solid material, or "puck" 1010, milled for an upper dental tray made from an FDA approved material. In one or more embodiments, the material being milled can be an Ethylene Propylene Copolymer or a Polyoxymethlene Copolymer. In other embodiments, the material can be an thermoplastic olefin, thermoplastic polyolefin, or olefinic thermoplastic elastomer. As one of skill in the art will appreciate, different materials can be turned into "pucks" for milling.

During the process, the button protrusions 1010 are milled as shown in 1020. Next, as shown in 1030, the upper dental tray of a dental appliance is milled from the puck. The bottom dental tray can be milled in a similar process. Thus, the dental appliance can be milled such that the button protrusions and/or the dental pads on the lower dental tray are part of one homogeneous dental tray by direct manufacturing independent of later gluing or cementing of the button protrusions and bite pads.

Thus, as shown above, the upper and lower dental trays of a dental appliance can be directly manufactured using a milled process, injection molded process and/or 3D technology. Material appropriate for injection molding of dental appliances include thermoplastics, thermoplastic elastomers and the like. In one or Ethylene Propylene Copolymer or a Polyoxymethlene Copolymer. In other embodiments, the material can be an thermoplastic olefin, thermoplastic polyolefin, or olefinic thermoplastic elastomer Material appropriate for 3D printing technology include thermoset polymers such as light polymerizable liquid materials. In one or more embodiments, the material appropriate for 3D printing includes a crosslinked polymer, such as a polyurethane, a methacrylate or a copolymer. In some embodiments, 3D printing materials can include nylon materials.

In one or more embodiments, the materials used for milling and/or injection molding can be provided by Myerson Tooth, Inc., including VisiClear™, and DuraFlex™, which are Ethylene Propylene Copolymers having the following properties as shown in Table 1:

TABLE 1

| | Test Method | Nominal Value Unit |
|---|---|---|
| Physical | | |
| Density-Specific Gravity (Method B) | ASTM D792 | .902 sp gr 23/23° C. |
| Melt Mass-Flow Rate (MFR) | ASTM D1238 | 40 g/10 min |
| Mechanical | | |
| Tensile Strength @ Yield | ASTM D638 | 4060 psi |
| Tensile Elongation @ Yld | ASTM D638 | 12.00% |
| Flexural Modulus (Procedure A) | ASTM D790 | 1% Secant: 145000 psi |
| Impact | | |
| Notched Izod Impact (73° F.) | ASTM D256 | .0899 ft lb/in |
| Thermal | | |
| DTUL @ 66 psi - Unannealed | ASTM D648 | 194° F. |
| Optical | | |
| Haze | ASTM D1003 | 6.00% |

In another embodiment, the milled or the injection molding material can be provided by DuraCetal™, also available from Myerson Tooth, Inc., which is a Polyoxymethlene Copolymer with the following properties shown in Table 2:

TABLE 2

| | Test Method | Nominal Value Unit |
|---|---|---|
| Physical | | |
| Specific Gravity | ASTM D792 | 1.41 |
| Melt Mass-Flow Rate (MFR) | ASTM D1238 | |
| Mechanical | | |
| Tensile Strength | ASTM D638 | 8800 psi |
| Tensile Elongation | ASTM D638 | 60.00% |
| Flexural Modulus | ASTM D790 | .38 psi × $10^6$ |
| Impact | | |
| Impact Strength, Izod, notched ⅛ in (3.18 mm) section | ASTM D256 | 1 ft-lb/in |
| Thermal | | |
| Deflection Temperature @ 264 psi (1.82 Mpa) | ASTM 648 | |
| Deflection Temperature @ 66 psi (0.45 Mpa) | ASTM D648 | 315 ƒC |

Figure 11:
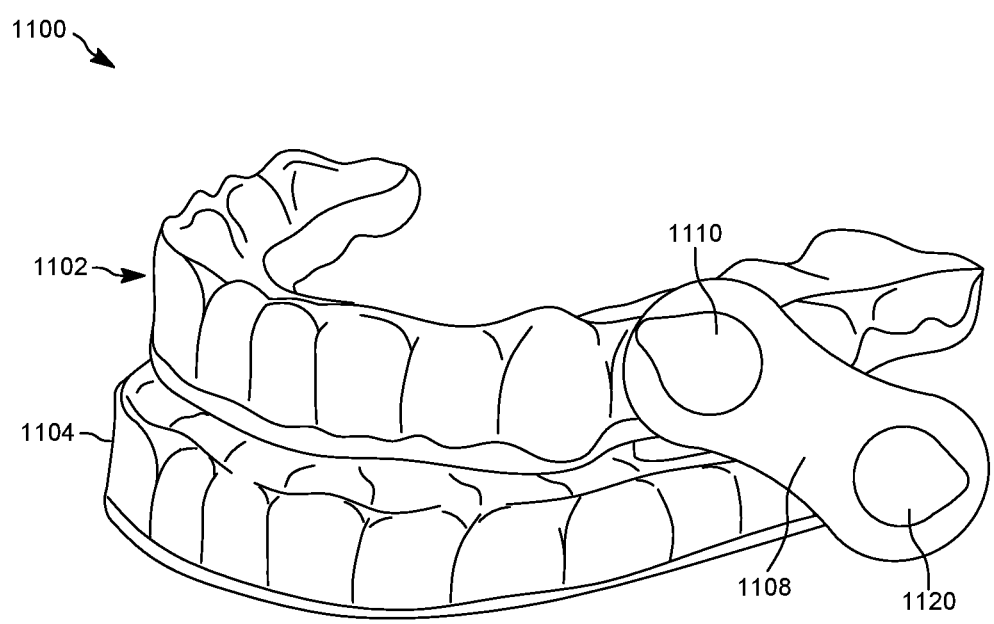
FIG. 11 illustrates a dental appliance with elastic bands attached in accordance with an embodiment of the present disclosure.

Referring now to FIG. 11, dental appliance 1100 is illustrated with an upper dental tray 1102 and lower dental tray 1104 with elastic bands connecting either side of the dental appliance. As shown, on a left side of the dental appliance, an elastic band 1108 is shown connecting button protrusion button 1110 and 1120.

The resulting dental appliance, from injection molding, milling, or 3D printing beneficially does not require added components other than elastic bands as shown in FIG. 11 because dental appliance is direct manufactured such that the button protrusions and mandibular bite pads do not have to be added later, but homogeneously included in molds, milled pucks or via a 3D generation machine. Prior to the direct manufacturing as disclosed herein, dental trays required different components such as button protrusions and bite pads to be added by gluing or the like or encased in a thermoforming (nonmilled) method.

Because direct manufacturing requires placement of button protrusions and bite pads during manufacture of the dental appliance as a whole, the measurements for determining where the button protrusions and the bite pads for each patient are determined prior to the making of the homogeneous dental trays. Referring back to FIG. 1A, scanner/camera 16, in one embodiment, includes a determination of the necessary oral characteristic data, including dentition data, which can include teeth data and soft palate data, to determine proper placement of button protrusions and bite pads.

In one or more embodiments, a method includes determining the amount of vertical component, or height of bite pads for the dental appliance as a function of the shape of the soft palate. In other embodiments, the vertical displacement is determined by the soft tissue of the patient, such as the hyoid shape. In one or more embodiments, a scanner and/or camera such as scanner/camera 16 detects shape of soft palate. The data is collected as oral characteristic data and provided to a processor which operates to classify the oral characteristics for fabrication of the homogeneous appliance.

In one or more embodiments, there are three classifications for a soft palate: short, normal or long. Thus, in one or more embodiments, a method includes determining if the posterior edge of the soft palate is short. For example, if there is about 5 to 7 mm of space between the posterior edge of the soft palate to the posterior wall of the oral pharynx, the soft palate is determined to be short, and a dental appliance will need about 5 to 7 mm of vertical displacement. In some embodiments, to determine the vertical displacement, a scanner can measure the distance from the gingival-tooth crown juncture of the maxillary central to the gingival-tooth crown juncture of the mandibular central. If this distance is, for example, 20 mm and, thus, 7 mm of vertical is desired, in some embodiments, a vertical displacement can be determined such that the bite will have 7 mm of vertical displacement.

In some embodiments, a method includes determining if the posterior edge of the soft palate is longer than a normal soft palate. If the soft palate is longer such that the posterior edge of the soft palate has 3 to 4 mm of space between it and the posterior wall of the oral pharynx, in some embodiments, a dental appliance can be made to provide 8 to 10 mm of vertical displacement to keep the soft palate from closing the airway when the patient in a supine position.

If the soft palate is very long and webbed shaped with just 2 mm or less of space between the soft palate and the posterior wall of the oral pharynx, the appliance will likely require 11 to 14 mm of vertical. displacement.

In one or more embodiments, a scanner determines whether a soft palate is short, long or normal and determines the placement of the uvula with respect to the palate. FIGS. 12-17 illustrate possible scanned illustrations of patient soft palates.

Figure 12:
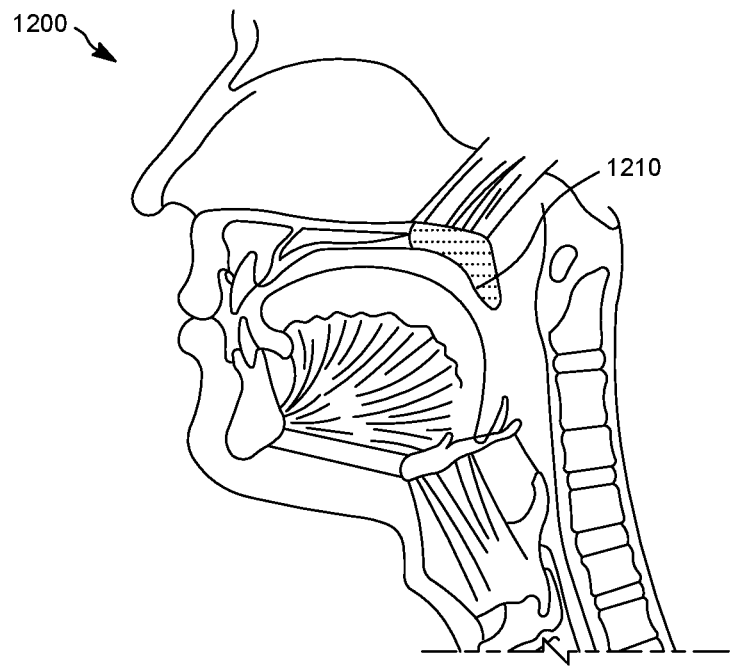
FIG. 12 illustrates a profile of a patient's oral cavity illustrating a short soft palate in accordance with one or more embodiments of the present disclosure.
Figure 13:
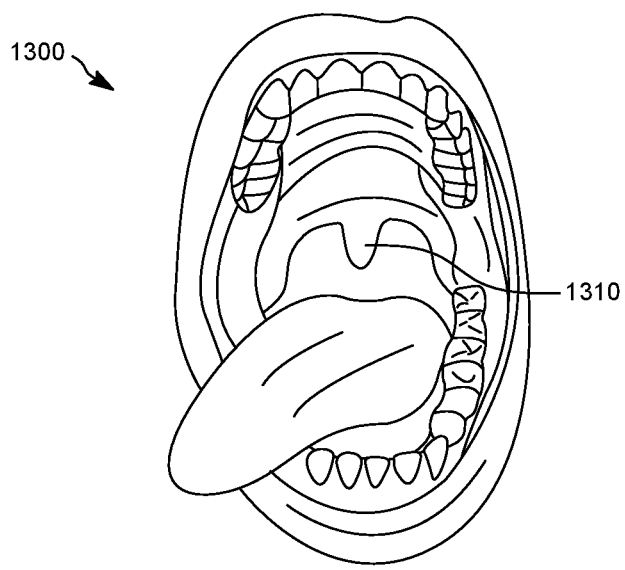
FIG. 13 illustrates an open mouth of a patient illustrating a normal soft palate and uvula in accordance with one or more embodiments of the present disclosure.

Referring to FIGS. 12 and 13, a profile of a patient's head 1200 and an open mouth of a patient 1300 are illustrated. FIG. 12 illustrates a short palate 1210. FIG. 13 illustrates the same short palate 1310 from a front perspective.

Figure 14:
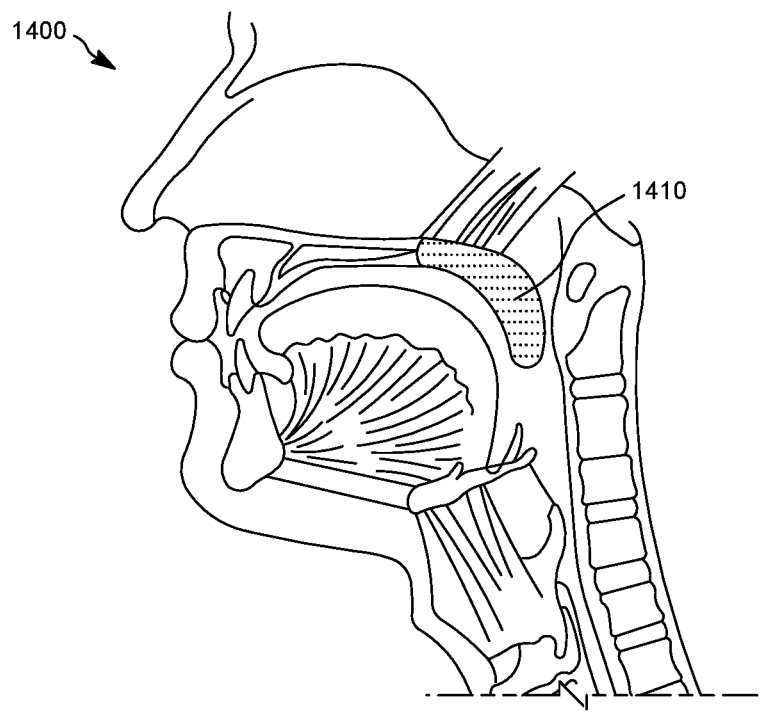
FIG. 14 illustrates a profile of a patient's oral cavity illustrating a normal soft palate in accordance with one or more embodiments of the present disclosure.
Figure 15:
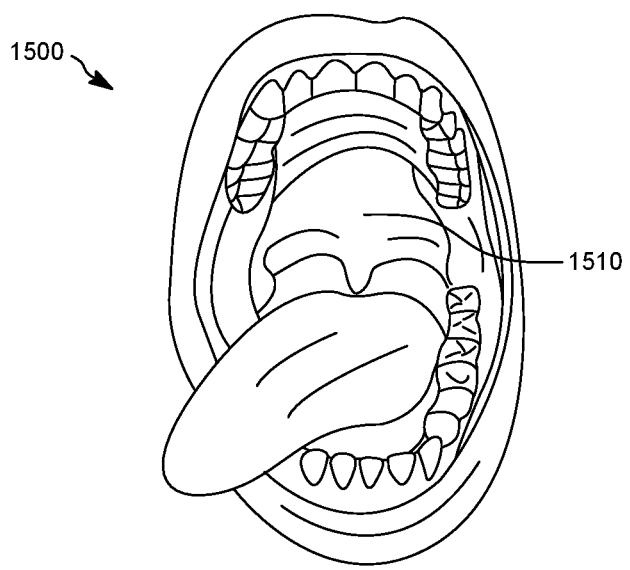
FIG. 15 illustrates an open mouth of a patient illustrating a long soft palate and uvula in accordance with one or more embodiments of the present disclosure.

FIG. 14 illustrates profile 1400 and a normal palate 1410 of a patient. FIG. 15 illustrates an open mouth 1500 of a patient and a front perspective of a normal palate 1510.

Figure 16:
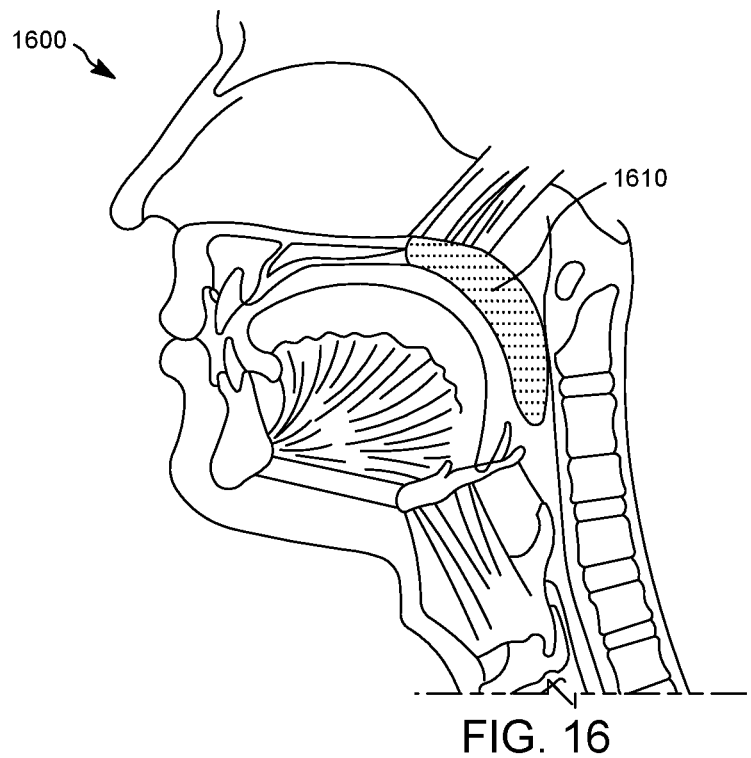
FIG. 16 illustrates a profile of a patient's oral cavity illustrating a long soft palate in accordance with one or more embodiments of the present disclosure.
Figure 17:
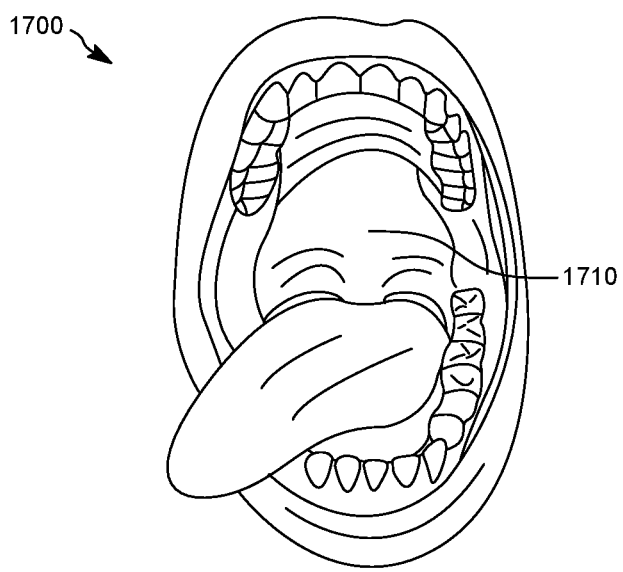
FIG. 17 illustrates an open mouth of a patient illustrating a long soft palate and uvula in accordance with one or more embodiments of the present disclosure.

FIG. 16 illustrates profile 1600 and a long palate 1610 of a patient. FIG. 17 illustrates an open mouth 1700 of a patient and a front perspective of a long palate 1710.

The determination of whether a palate is short, normal or long can be made by a dental professional through examination, or, in accordance with an embodiment, via scanner/camera 16 collecting data related to the patient.

Determining the placement and size of the lower dental tray bite pads is a function of the length of the palate of a patient. Additionally, in some embodiments, maxillary button protrusions on an upper dental tray are placed on each incisal edge, in the embrasure between the right and left cuspids and first bicuspids.

The placement of the mandibular button protrusions can be determined by determining a patient's range of motion. In some embodiments, a scanner detects maximal range of motion by measuring before and after extension of the lower jaw. For example, if the patient has only 5-7 mm of potential advancement, the buttons are placed 23 mm apart with the patient's teeth in centric. If the patient has 7-10 mm of potential advancement, the buttons are placed 25 mm apart, and if the patient has 10-17 mm of potential advancement, the buttons are placed 27 mm apart.

In one or more embodiments, a method includes determining the location of the buttons on the mandibular arch by occluding the patient's models in centric and placing the center of the mandibular button 23, 25, or 27 mm from the center of the maxillary button.

As described above, a scanner/camera takes images/scans of a patient's mouth to determine dentition data and soft tissue data, such as soft palate data and a computer system coupled to the scanner or processor incorporated into a scanner/camera determines the placement of the button protrusions and bite pads as described above.

Figure 18:
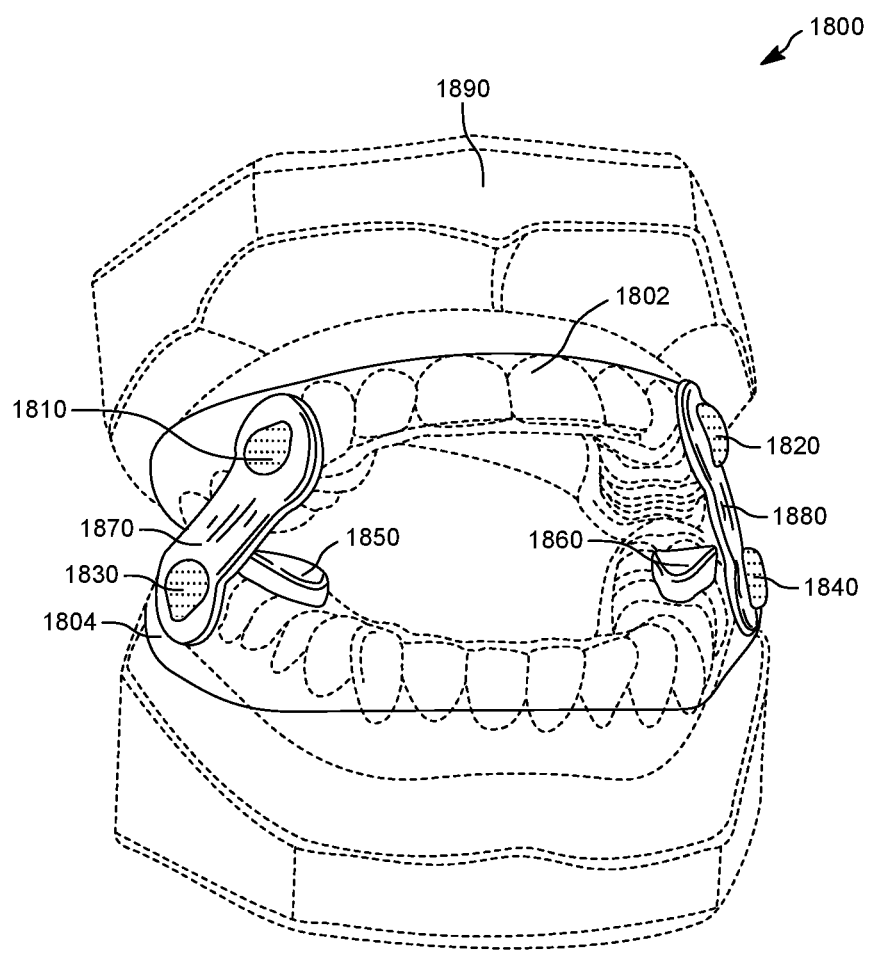
FIG. 18 illustrates a dental appliance disposed on a mold of a patient's teeth in an open position in accordance with one or more embodiments of the present disclosure.

Referring now to FIG. 18, an illustration of a dental appliance in accordance with embodiments herein is shown. More particularly, dental appliance 1800 includes an upper dental tray 1802, a lower dental tray 1804, four button protrusions 1810, 1820 disposed on the upper dental tray 1802, and button protrusions 1830, 1849 disposed on the lower dental tray 1804. Lower dental tray 1804 also is shown including vertical displacement bite pads 1850 and 1860. In one embodiment, the dental appliance includes elastic bands 1870 and 1880 disposed on either side of the dental appliance to couple the upper dental tray 1802 to the lower dental tray 1804.

Also illustrated in FIG. 18 is a model 1890 which includes a patient's teeth. The model can be formed from a scan of a patient and 3D printed or from molds of a patient's teeth.

In one or more embodiments, the dentition data includes gum line data to enable retention of the dental appliance for the patient. More specifically, an appliance can be better retained if the trays are designed to fit at the gum line. Thus, in some embodiments, a method includes determining a 3 millimeter distance below a tooth crown-gingival junction on the upper dental tray unless there is a protrusive axial inclination of the incisors. For protrusive axial inclinations of incisor patients, the upper dental tray is formed to reach one third to one half the way up on the anterior teeth. The lower dental tray is formed to reach 3 millimeters below a tooth crown-gingival juncture unless a patient's mandibular incisors also have a protrusive axial inclination. For protrusive axial inclination of mandibular incisor patients, the lower dental tray is formed to reach above the tooth crown-gingival area at the anterior incisors. The gum line data is provided to form the dental trays in 3D model prior to using either milling process or prior to use of mold.

As described above, a dental appliance as shown in FIG. 18 is formed by, in one or more embodiments, a method including receiving oral characteristic data of a patient; processing the oral characteristic data in a server to determine dentition data, a vertical displacement and a forward mandibular position to enable the patient to breathe during sleep by opening an airway of the patient; and forming a dental appliance via direct manufacture using the dentition data, the vertical displacement and the forward mandibular position, the dental appliance including a lower dental tray and an upper dental tray, each of the lower dental tray and the upper dental tray being homogeneous, the lower dental tray inclusive of a vertical displacement bite pad with the vertical displacement and a first pair of button protrusions, the upper dental tray inclusive of a second pair of button protrusions, the first pair of button protrusions and the second pair of button protrusions providing the forward mandibular position when two elastic bands are attached to connect the upper dental tray and the lower dental tray.

In one or more embodiments, the dental appliance is formed by three-dimensional (3D) printing of one or more of a light polymerizable liquid thermoset crosslinked polymer, a polyurethane, a methacrylate or a copolymer.

In one or more embodiments, the dental appliance is formed by three-dimensional (3D) printing of a polymerizable resin composition of a urethane monomer of urethane dimethacrylate (UDMA), an acidic monomer, and one or more hydrophobic monomers.

In one or more embodiments, the dental appliance is milled or injection molded from one or more of an Ethylene Propylene Copolymer and a Polyoxymethlene Copolymer.

In one or more embodiments, the dental appliance is injection molded using a thermoplastic olefin, thermoplastic polyolefin, or olefinic thermoplastic elastomer.

In one or more embodiments receiving oral characteristic data of the patient includes scanning by a scanner or camera a mold of the teeth; and transmitting the oral characteristic data to a server.

In one or more embodiments receiving oral characteristic data of a patient includes scanning by a scanner of an oral cavity of the patient; imaging the oral cavity to determine the dentition data, wherein the oral characteristic data includes dentition data as one or more images of teeth and a gum line of the patient and one or more images of a soft palate of the patient; and transmitting the oral characteristic to a server.

In one or more embodiments the method includes determining via the oral characteristic data the vertical displacement as a function of a shape of the soft palate of the patient.

In one or more embodiments the determining via the oral characteristic the vertical displacement as a function of the shape of the soft palate of the patient includes determining a vertical displacement of between 5 and 7 millimeters if the soft palate has between 5 to 7 millimeters of space between a posterior edge of the soft palate to a posterior wall of an oral pharynx of the patient.

In one or more embodiments, the determining via the oral characteristic data the vertical displacement as a function of the shape of the soft palate of the patient includes processing the oral characteristic data to measure a distance from a gingival-tooth crown juncture of a maxillary central to a gingival-tooth crown juncture of a mandibular central.

In one or more embodiments the determining via the oral characteristic data the vertical displacement as a function of the shape of the soft palate of the patient includes determining if a posterior edge of the soft palate is longer than a normal soft palate with between 3 and 5 millimeters of space between a posterior edge of the soft palate to a posterior wall of an oral pharynx of the patient; and providing the vertical displacement of between 8 and 10 millimeters.

In one or more embodiments the determining via the oral characteristic data the vertical displacement as a function of the shape of the soft palate of the patient includes determining if a posterior edge of the soft palate is longer than a normal soft palate and webbed and wherein two millimeters or less of space exists between the soft palate and a posterior wall of an oral pharynx, providing at least 11 to 14 millimeters for the vertical displacement.

In one or more embodiments the determining via the oral characteristic data the vertical displacement as a function of the shape of the soft palate of the patient includes determining whether the soft palate is one of short, normal, and long.

In one or more embodiments the lower dental tray is inclusive of a first vertical displacement bite pad on a left side of the lower dental tray and a second vertical displacement bite pad on a right side of the lower dental tray wherein a height of each of the first and second vertical displacement bite pads is determined according to the oral characteristic data, the oral characteristic data providing soft tissue data of the patient indicative of airway function.

In one or more embodiments the vertical displacement is provided by a thickness of the lower dental tray.

Another embodiment is directed to a system including a processor and a non-transitory computer-readable storage medium storing instructions operative when executed on the processor to perform a method including receiving oral characteristic data of a patient; processing the oral characteristic data in a server to determine dentition data, a vertical displacement and a forward mandibular position to enable the patient to breathe during sleep by opening an airway of the patient; and forming a dental appliance via direct manufacture using the dentition data, the vertical displacement and the forward mandibular position, the dental appliance including a lower dental tray and an upper dental tray, each of the lower dental tray and the upper dental tray being homogeneous, the lower dental tray inclusive of the vertical displacement and a first pair of button protrusions, the upper dental tray inclusive of a second pair of button protrusions, the first pair of button protrusions and the second pair of button protrusions providing the forward mandibular position when two elastic bands are attached to connect the upper dental tray and the lower dental tray.

Another embodiment is directed to a method including receiving, by a server, one or more data sets associated with a patient; determining, by the server one or more positions for placement of button protrusions based on the received data sets from a scanner, the received data sets including at least a dentition pattern, a gum line measurement, a palate measurement of a soft palate shape of the patient and a uvula placement measurement with respect to the palate shape of the patient; communicating, by the server the one or more positions for placement of button protrusions and a vertical displacement, the communicating including assigning a value associated with each of the one or more positions for placement of button protrusions, each value representative of a distance between an upper tray button protrusion and a lower tray button protrusion for mandibular advancement; transmitting the value data to one or more of a three-dimensional printer, a milling apparatus and an injection molding apparatus; forming a dental appliance via direct manufacture using the value associated with each of the one or more positions for placement of button protrusions, the dental appliance including a lower dental tray and an upper dental tray, each of the lower dental tray and the upper dental tray being homogeneous, the lower dental tray inclusive of the vertical displacement and a first pair of the button protrusions, the upper dental tray inclusive of a second pair of the button protrusions, the first pair of button protrusions and the second pair of button protrusions providing the forward mandibular position when two elastic bands are attached to connect the upper dental tray and the lower dental tray.

In one or more embodiments, the dental appliance is formed by three-dimensional (3D) printing of one or more of a light polymerizable liquid thermoset crosslinked polymer, a polyurethane, a methacrylate and a copolymer.

In one or more embodiments, the dental appliance is one or more of milled and injection molded using one or more of an Ethylene Propylene Copolymer and a Polyoxymethlene Copolymer.

In one or more embodiments, the dental appliance is formed by three-dimensional (3D) printing of a polymerizable resin composition of a urethane monomer of urethane dimethacrylate (UDMA), an acidic monomer, and one or more hydrophobic monomers.

In one or more embodiments, the dental appliance is injection molded using a thermoplastic olefin, thermoplastic polyolefin, or olefinic thermoplastic elastomer.

In one or more embodiments, the vertical displacement is a function of the soft palate shape of the patient.

In one or more embodiments, the vertical displacement is provided by one or more of a pair of bite pads on the lower dental tray or by a thickness of the lower dental tray.

In one or more embodiments, the gum line determination identifies a maxillary tooth crown-gingival junction and a mandibular tooth crown-gingival junction, the upper dental tray is formed to reach about a three millimeter distance below the maxillary tooth crown-gingival junction on the upper dental tray, and the lower dental tray is formed to reach about three millimeters below the mandibular tooth crown-gingival junction.

Another embodiment is directed to a system including a processor and a non-transitory computer-readable storage medium storing instructions operative when executed on the processor to perform a method including receiving, by a server, one or more data sets associated with a patient; determining, by the server one or more positions for placement of button protrusions based on the received data sets from a scanner, the received data sets including at least a dentition pattern, a palate measurement of a soft palate shape of the patient and a uvula placement measurement with respect to the palate shape of the patient; communicating, by the server the one or more positions for placement of button protrusions and a vertical displacement, the communicating including assigning a value associated with each of the one or more positions for placement of button protrusions, each value representative of a distance between an upper tray button protrusion and a lower tray button protrusion for mandibular advancement; transmitting the value data to one or more of a three-dimensional printer, a milling apparatus and an injection molding apparatus; forming a dental appliance via direct manufacture using the value associated with each of the one or more positions for placement of button protrusions, the dental appliance including a lower dental tray and an upper dental tray, each of the lower dental tray and the upper dental tray being homogeneous, the lower dental tray inclusive of the vertical displacement and a first pair of the button protrusions, the upper dental tray inclusive of a second pair of the button protrusions, the first pair of button protrusions and the second pair of button protrusions providing the forward mandibular position when two elastic bands are attached to connect the upper dental tray and the lower dental tray.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

What is claimed:
1. A method comprising:
  receiving, by a server, one or more data sets associated with a patient;
  determining, by the server one or more positions for placement of button protrusions based on the received data sets from a scanner, the received data sets including at least a dentition pattern, and a gum line of the patient;

communicating, by the server the one or more positions for placement of button protrusions and a vertical displacement, the communicating comprising:

assigning a value associated with each of the one or more positions for placement of button protrusions, each value representative of a distance between an upper tray button protrusion and a lower tray button protrusion for mandibular advancement;

transmitting the value data to one or more of a three-D printer, a milling apparatus and an injection molding apparatus;

forming a dental appliance via direct manufacture using the value associated with each of the one or more positions for placement of button protrusions, the dental appliance including a lower dental tray and an upper dental tray, each of the lower dental tray and the upper dental tray being homogeneous, the lower dental tray inclusive of the vertical displacement and a first pair of the button protrusions, the upper dental tray inclusive of a second pair of the button protrusions, the first pair of button protrusions and the second pair of button protrusions providing the forward mandibular position when two elastic bands are attached to connect the upper dental tray and the lower dental tray.

2. The method of claim 1 wherein the dental appliance is formed by three-dimensional (3D) printing of one or more of a light polymerizable liquid thermoset crosslinked polymer, a polyurethane, a methacrylate and a copolymer.

3. The method of claim 1 wherein the dental appliance is one or more of milled and injection molded using one or more of an Ethylene Propylene Copolymer and a Polyoxymethlene Copolymer.

4. The method of claim 1 wherein the dental appliance is formed by three-dimensional (3D) printing of a polymerizable resin composition of a urethane monomer of urethane dimethacrylate (UDMA), an acidic monomer, and one or more hydrophobic monomers.

5. The method of claim 1 wherein the dental appliance is injection molded using a thermoplastic olefin, thermoplastic polyolefin, or olefinic thermoplastic elastomer.

6. The method of claim 1 wherein the vertical displacement is a function of a soft palate shape of the patient.

7. The method of claim 1 wherein the vertical displacement is provided by one or more of a pair of bite pads on the lower dental tray or by a thickness of the lower dental tray.

8. The method of claim 1 wherein the gum line determination identifies a maxillary tooth crown-gingival junction and a mandibular tooth crown-gingival junction, the upper dental tray is formed to reach about a three millimeter distance below the maxillary tooth crown-gingival junction on the upper dental tray, and the lower dental tray is formed to reach about three millimeters below the mandibular tooth crown-gingival junction.

9. A system comprising a processor and a non-transitory computer-readable storage medium storing instructions operative when executed on the processor to perform the method of claim 1.

10. The method of claim 1 wherein the received data sets include a palate measurement of a soft palate shape of the patient and a uvula placement measurement with respect to the soft palate shape of the patient.

* * * * *